United States Patent [19]

Barr

[11] 4,252,538
[45] Feb. 24, 1981

[54] APPARATUS AND METHOD FOR ANTIBODY SCREENING, TYPING AND COMPATIBILITY TESTING OF RED BLOOD CELLS

[75] Inventor: Lawrence D. Barr, Tucson, Ariz.

[73] Assignee: Engineering & Research Associates, Inc., Tucson, Ariz.

[21] Appl. No.: 16,805

[22] Filed: Mar. 2, 1979

[51] Int. Cl.³ .................. G01N 35/02; G01N 33/54; G01N 33/80
[52] U.S. Cl. .................. 23/230 B; 422/61; 422/68; 422/72; 422/102; 424/11; 424/12; 23/915
[58] Field of Search .............. 23/230 B; 422/61, 68, 422/72, 102; 424/11, 12

[56] References Cited

U.S. PATENT DOCUMENTS

| | | | |
|---|---|---|---|
| 3,432,275 | 3/1969 | Unger | 424/11 |
| 3,532,470 | 10/1970 | Rochte | 422/61 |
| 3,540,857 | 11/1970 | Martin | 422/61 X |
| 3,713,780 | 1/1973 | Shapiro | 422/61 |
| 3,715,189 | 2/1973 | Nighohossian | 422/61 |
| 3,771,965 | 11/1973 | Grams | 422/72 |
| 3,826,622 | 7/1974 | Natelson | 422/72 X |
| 4,055,394 | 10/1977 | Friedman | 424/11 X |
| 4,066,407 | 1/1978 | Lupica | 422/72 X |
| 4,119,407 | 10/1978 | Goldstein | 422/61 X |

Primary Examiner—Sidney Marantz
Attorney, Agent, or Firm—Cahill, Sutton & Thomas

[57] ABSTRACT

A dual cavity substrate having a sample compartment for selectively discharging the fluid under test is rotatably mounted in a holder. A monolayer of red blood cells is centrifugally developed on the cavity surfaces of the substrate and, after typing, is subjected to the presence of an antibody which antibody may or may not have an affinity for the antigen of the first layer of red blood cells. A second monolayer of red blood cells is layed on the antibody. One of the two layers of blood cells or the antibody is the element being tested. Should agglutination of the second layer of red blood cells occur, the test is positive. Equipments for various substrate surface preparation procedures as well as for washing, lysing and optical inspection procedures are also described. A method for conducting various tests performable by the apparatus is disclosed.

57 Claims, 13 Drawing Figures

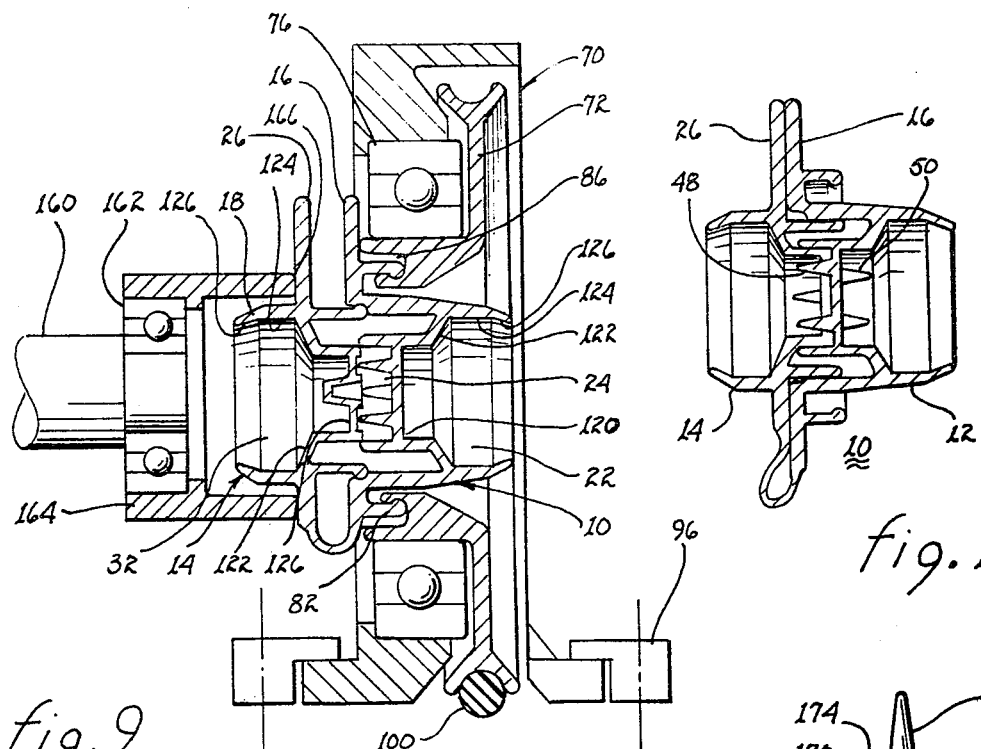
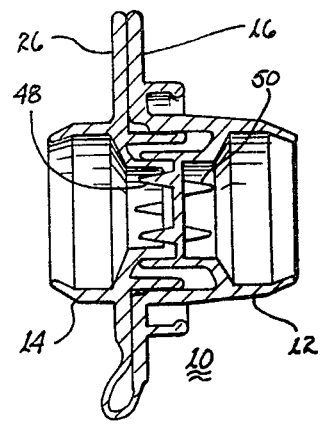
fig. 10
fig. 9
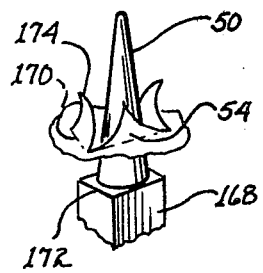
fig. 11
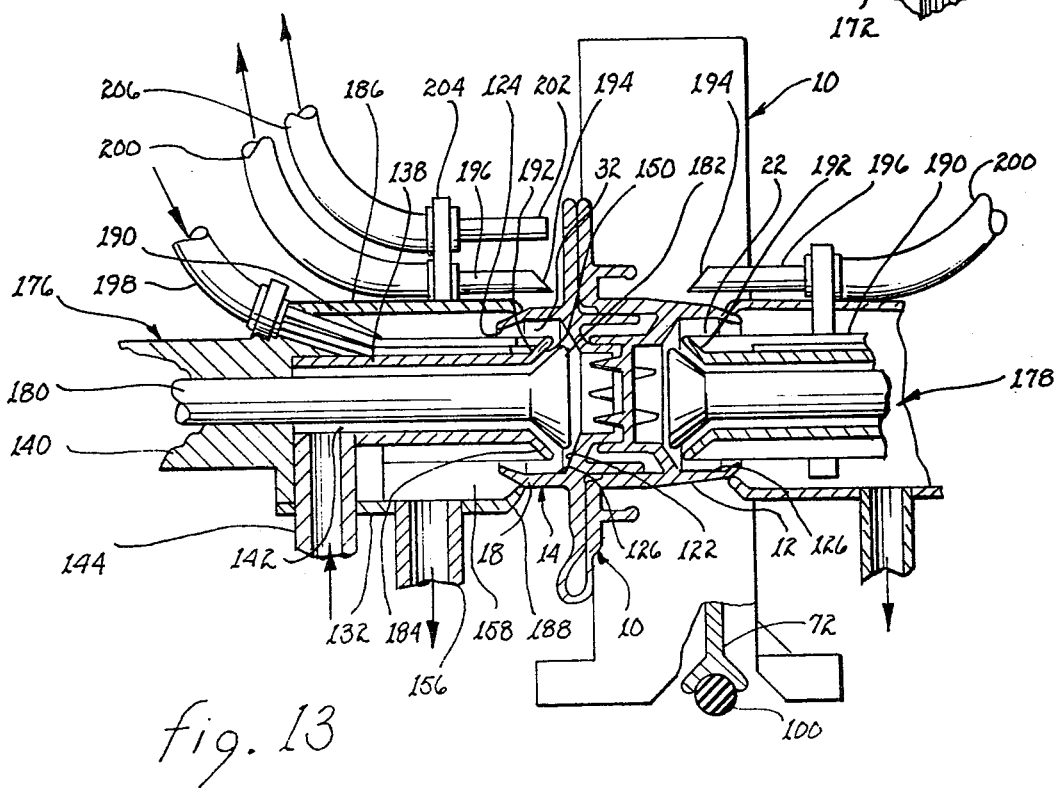
fig. 13

APPARATUS AND METHOD FOR ANTIBODY SCREENING, TYPING AND COMPATIBILITY TESTING OF RED BLOOD CELLS

The present invention relates to blood testing and, more particularly, to apparatus for automatically testing red blood cells.

A process known as the Rosenfield-Kochwa or the Rosenfield process is a special sequence of operations for antibody screening, blood typing or blood compatibility testing. In essence, the process will produce information about the affinity of an antibody to the antigens of layers of red blood cells sandwiching the antibody. The unknown element may be either of the layers of red blood cells or the antibody.

Antibody screening, blood typing and compatibility tests under the Rosenfield process depend primarily on the fact that blood cells tend to clump together or agglutinate in the presence of antibodies which can attach themselves to blood cell surfaces. The antibodies literally act as bonding links between adjacent cells to form clumps of cells. However, an antibody will attach itself to a blood cell only if that cell has a specific molecular site, called antigen, on its surface with an affinity for the antibody. The kind and number of these antigens characterize the blood cells.

The apparatus described hereinafter includes a spinning substrate upon which a first monolayer of red blood cells is disposed. The first monolayer is lysed or bleached of its red hemoglobin by ejecting a solution (nominally distilled water) upon the first monolayer. A fluid, (such as plasma) containing an antibody, is spread upon the first monolayer and bonding therebetween will result if the antibody reacts with the antigen of the first monolayer of red blood cells. A second monolayer of red blood cells is deposited upon the fluid and bonding with the antibody will result if the antigens of the second layer have an affinity for the antibody. If the antibody bonds to the antigens of both monolayers, agglutination will occur and the test will be positive and indicate the reaction. Optical inspection means provides an indication of agglutination by detecting the presence of a reddish tint due to bonding of the second monolayer despite a washing of the substrate. Further means are included for dispensing substances to prepare the substrate surface, lysing the first monolayer, and periodic washing/rinsing. Accordingly, the procedure of agglutinating red blood cells provides information about the cells or the fluid depending upon how the testing is conducted. Moreover, the degree of agglutination that occurs is a further means for classifying a sample under test. That is, the more the blood cells agglutinate, the more positive the test becomes which is also a measure of the strength of the antigen-antibody reaction.

Depending on whether the testing is blood typing, blood compatibility testing or antibody screening, one of the first or second monolayers or the fluid may be the unknown substance and the remaining two are reagents. The substrate itself may include a test cavity and a control cavity wherein the steps are performed while the substrate is spinning. The substrate may also include a sample compartment wherein the unknown substance is stored until it is to be dispensed into the test and control cavity. Dispensation means is also described for effecting timely dispensation of the unknown substance.

All of the above may be performed by manual command or by automated procedures to minimize the possibility of human error.

Is is therefore a primary object of the present invention to provide automated apparatus for carrying out the Rosenfield process for blood testing.

Another object of the present invention is to provide a spinning substrate for blood typing, blood compatibility testing and antibody screening.

Yet another object of the present invention is to provide a spinning substrate for blood and serum testing which includes a test cavity and a control cavity.

Still another object of the present invention is to provide a spinning substrate for blood testing which incorporates a sealed compartment from which a sample under test is ejected into a test cavity and a control cavity.

A further object of the present invention is to provide a means for ejecting various fluids upon the surface of a spinning substrate.

A yet further object of the present invention is to provide light sensitive scanning means for detecting the presence of color in a sample disposed upon the surface of a spinning substrate.

A still further object of the present invention is to provide a method for carrying out the steps of the Rosenfield process for blood testing.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 9 illustrates apparatus for releasing the sample under test from within the substrate;

FIG. 10 illustrates the substrate in its compressed configuration;

FIG. 11 illustrates the piercing action of the prongs within the substrate;

FIG. 13 illustrates apparatus for rinsing and optically inspecting and reading the substrate.

A whole blood test sample from a donor is prepared for typing by removal of all but the red cells. The primary reason for removal of the plasma and the white cells is that the plasma may contain antibodies which could produce confusing final results. Separation of the red blood cells may be effected by centrifuging the blood sample, which centrifuging places the red blood cells at the bottom of the container due to their greater specific gravity. The plasma and white blood cells may be removed by conventional means, such as with a suction probe. The red blood cells are washed and rinsed by filling the container with a normal saline solution, agitating the container to stir the cells into solution and then centrifuging the mixture to separate the cells from the solution. Usually three wash or rinse cycles are sufficient if the saline solution volume is approximately twenty-five times the volume of the red blood cells. The term "normal saline solution" is used hereinafter to denote a solution of distilled water and salt (NaCl) to render it equal in salinity to the fluid in the red blood cells. If the solution differs in salinity, the cell membrane will rupture and the hemoglobin will be released, destroying the cell.

After the red blood cells have been adequately cleaned, they may be optionally treated with a special enzyme solution or its equivalent. This treatment consists of mixing the red blood cells and enzyme solution and allowing an appropriate waiting or incubation period before separation of the cells from the solution. Separation is done by centrifuging in the manner described above. The treatment of the red blood cells with an enzyme solution sensitizes the surface of the red blood cells to make them more reactive to antibody treatment. On completion of the treatment with the enzyme solution, the red blood cells are again rinsed three or more times with a normal saline solution to remove the enzyme solution.

After final rinsing, the red blood cells are diluted with a normal saline solution to improve fluidity of the mixture. The dilution is fairly substantial in that only a small percentage by volume of the red blood cells will be used for testing.

Figure 1:
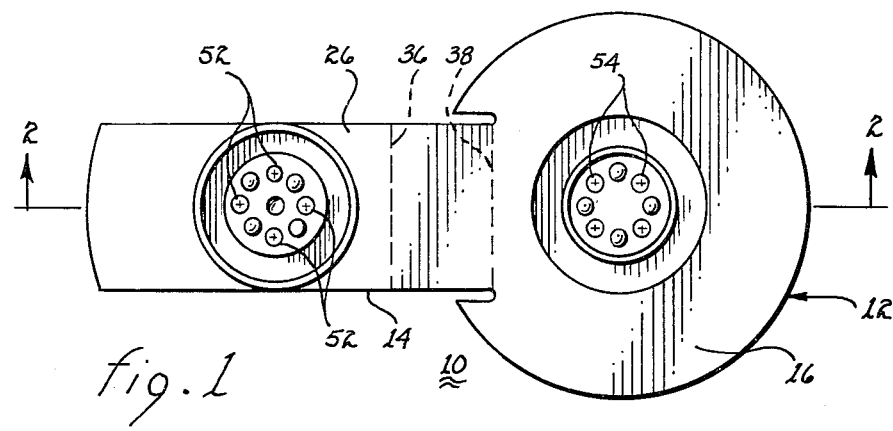
FIG. 1 is a plan view of a substrate.
Figure 2:
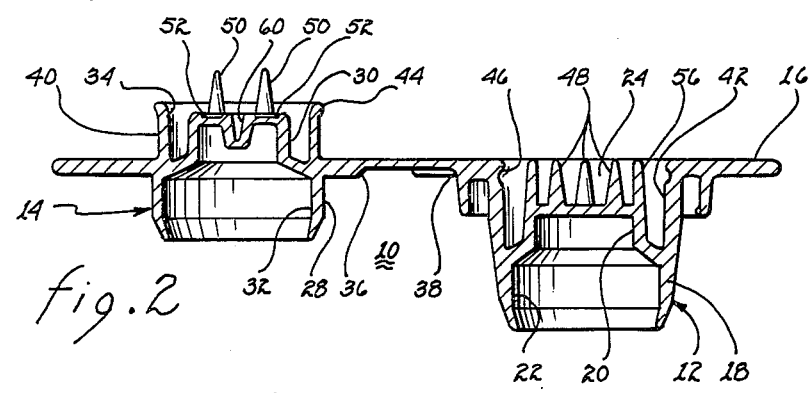
FIG. 2 is a cross-sectional view taken along lines 2—2, as shown in FIG. 1.

A substrate 10, which may be used, is illustrated in FIGS. 1 and 2. Substrate 10 is developed from a single piece of plastic material bifurcated into two connected parts 12 and 14. Part 12 includes a generally annular flange 16 having a cylindrical wall 18 depending therefrom. A membrane 20, extending across the interior of cylindrical wall 18, divides the interior volume defined by the cylindrical wall into test cavity 22, sample compartment 24 and annular recess 42.

Part 14 includes a generally rectangular tab 26 extending from annular flange 16. The tab supports a cylindrical wall 28. A membrane 30 extends across the cylinder defined by cylindrical wall 28 to define control cavity 32. A circular wall segment 40 extends from the opposite side of tab 26 and defines annular recess 34.

Figure 3:
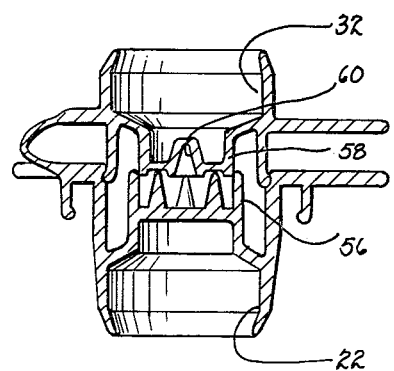
FIG. 3 is a cross-sectional view illustrating the mated halves of the substrate.

Referring particularly to FIG. 3 in combination with FIGS. 1 and 2, the mating relationship of parts 12 and 14 and operational characteristics of substrate 10 will be discussed. Parts 12 and 14 are mated to one another by bending tab 26 in the area defined by dashed lines 36 and 38. To facilitate bending, the cross-section of this portion of the tab may be reduced, as illustrated in FIG. 2. On bending of tab 26, wall segment 40 of part 14 interiorly mates with annular recess 42 within part 12. To maintain a mated connection, combing 44 is forced into annular depression 46 of the recess. This mating may be accomplished by a "snap action". Upon such mating, annular recesses 34 and 40 define a common sealed annular volume. Prongs 48, extending from membrane 20 are alternately meshed with prongs 50 extending from membrane 30 in a circular pattern, as illustrated in FIG. 1. The tips of each of these prongs positionally correspond with preweakened areas 52 and 54 in membranes 30 and 20, respectively.

Sample compartment 24 is defined by wall 56 extending from membrane 20 and sealingly mating with wall 58 defined by membrane 30. The opposed ends of compartment 24 are defined by the wall circumscribed sections of membranes 20 and 30.

By inspection, it will become apparent that part 12, excluding flange 16, is symmetrical about an axis orthogonal to flange 16. Similarly, part 14, excluding tab 26, is symmetrical about an axis orthogonal to the tab. By careful design of both the size and configuration of flange 16 and tab 26, substrate 10, as a whole, will be both statically and dynamically balanced about an axis defined by the axis of cylindrical walls 18 and 28 after parts 12 and 14 have been mated as shown in FIG. 3. Thus, substrate 10, as a unit, will be in balance about the axis of cylindrical walls 18 and 28.

Flange 16 serves several functions. First, it serves as an element for manipulating substrate 10 between various test stations; it serves as the means through which a spinning motion is imparted to the substrate and it serves as a base upon which identifying information, such as a bar code, is permanently attached.

Before proceeding further, it may be well to review the function and purpose of substrate 10 in the blood testing process under consideration. Test cavity 22 and control cavity 32 represent segregated cavities within which testing is effected. Sample compartment 24, which, after receipt of the sample of fluid to be tested, is sealed and remains sealed until membranes 20 and 30 are ruptured at areas 54 and 52 by prongs 50 and 48, respectively. Thereafter, the sample is ejected into the test and control cavities. After certain processes are conducted in the test and control cavities, an optical inspection is performed, which inspection renders a positive or negative test result.

Presently, it is contemplated that three types of tests can be carried out by the apparatus described herein. These test include: (a) blood typing, including forward and reverse typing; (b) antibody screening; and (c) compatibility testing.

In the following discussion of each of these types of tests, it will be presumed that substrate 10 is initially prepared as described to deposit an initial layer of BSA, a second layer of chromic chloride and that appropriate wash/rinse steps are conducted. Additionally, the various wash/rinse and inspection steps described are also to be conducted at appropriate intervals during testing.

For forward typing, the red blood cells to be tested are disposed within sample compartment 24 and discharged therefrom to develop a monolayer upon the test surfaces in both test cavity 22 and control cavity 32. This first monolayer is then lysed. Thereafter, a known antibody is disposed in the test cavity but not in the control cavity. A second monolayer of reagent (i.e. known) red blood cells is disposed in both the test and control cavities. By using a reagent red blood cell solution, bonding between the antigens of the reagent and the antibody will occur. Should the second monolayer of red blood cells wash away equally rapidly in both the test and control cavities, the test result will be negative as no bonding between the first monolayer of red blood cells and the antibody occurred.

Reverse typing contemplates the deposition of reagent red blood cells upon the test surfaces. The resulting monolayer of red blood cells is thereafter lysed. Serum to be tested and containing natural antibodies is discharged from sample compartment 24 into test cavity 22. A second monolayer of reagent red blood cells is deposited upon the serum. During inspection, the second monolayer of red blood cells will be washed away unless a reaction by both the first and second monolayers of red blood cells and the serum occurs.

The antibody screening test is procedurally similar to reverse typing. But the objectives are different. Reverse typing provides information that is normally used to confirm the results of forward typing. Antibody screening is done to detect the existence of an atypical antibody in the test serum/plasma. The procedure for performing antibody screening will be mechanically similar to the procedure for reverse typing except that the reagent cells will typically be different.

The compatibility test is directed to the function of mating a patient's blood with a donor's blood to determine whether a reaction therebetween will occur. A first monolayer of red blood cells from the donor is deposited in the test cavity and lysed. A sample of the patient's serum is discharged from sample compartment 24 into the test cavity. A second monolayer of blood cells from the donor are deposited in the test cavity. If, during the washing and inspection steps, the second monolayer is washed away, the results of the test will be negative.

The following description of the apparatus will be made with reference to forward typing of a sample of red blood cells. The red blood cell sample to be typed are channeled into compartment 24 of part 12 prior to the joining of parts 12 and 14. Commensurate therewith indicia for identification purposes is placed upon flange 16. After compartment 24 has received the sample, part 14 is mated with part 12 in the manner illustrated in FIG. 3. Should compartment 24 be overfilled, pressure relief is provided by the air chamber confined by conical depression 60 in part 14. Necessarily, appropriate sterilization of substrate 10 may be performed before filling to insure non-contamination of the sample.

In various steps to be undertaken in blood typing under the Rosenfield process, the time for each of the steps is substantially reduced if centrifugal force is employed in combination with dispensation of the various solutions.

Figure 4:
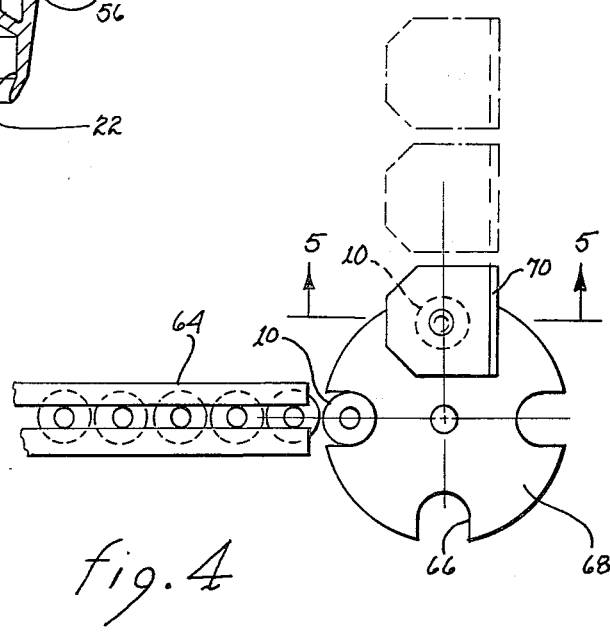
FIG. 4 is a pictorial view illustrating the loading of a substrate into a holder module.

Various means may be employed to impart rotation or spinning motion to substrate 10. FIG. 4 is therefore illustrative of only one type of apparatus which may be employed. A discharge chute 64 serially discharges each of substrates 10 into a retainingly receiving indentation 66 of a disc 68. At a station rotationally down stream from the station at which substrates 10 are ejected into disc 68, the substrates are mounted within modules 70. Each module, in essence, retains a substrate and, in cooperation with a power source, provides a means for imparting rotation to the substrate about an axis superimposed upon the axis of rotation of test and control cavities 22 and 23.

Figure 5:
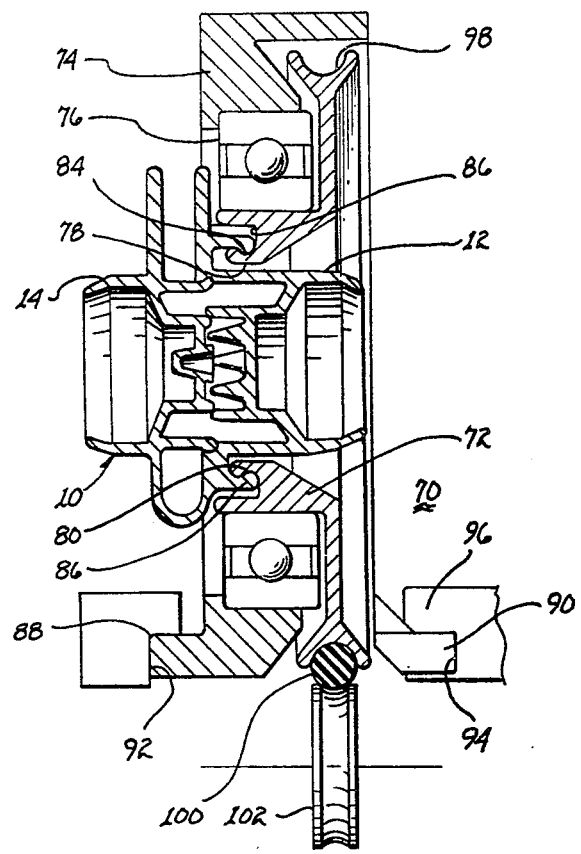
FIG. 5 is a cross-sectional view taken along lines 5—5, as shown in FIG. 4.

Referring to FIG. 5, module 70 includes a wheel 72 secured to a frame 74 by means of a bearing 76. Thereby, wheel 72 is rotatable with respect to frame 74. Substrate 10 is attached to the wheel by inserting part 12 through central aperture 78 of the wheel until combing 80 at the extremity of flange 82 seats within annular indentation 84 in annular recess 86 of the wheel. The mating may be referred to as a "snap action". Thus, rotation of wheel 72 will produce a commensurate rotation of substrate 10 about the common axis extending through test and control cavities 22 and 32.

Frame 74 includes at the base thereof laterally extending feet 88 and 90, which feet slidably mate with commensurate slots 92 and 94 disposed within a guide way 96. The guideway guides modules 70 to each of a plurality of work stations. Wheel 72 includes an annular groove 98 in the manner of a pulley for engagement with a drive belt 100. Translation of the drive belt may be effected by pulley 102 or the like. Thereby, translation of drive belt 100 will result in rotation of wheel 72 which in turn will spin substrate 10 during translation of module 70 along guide way 96.

Figure 6:
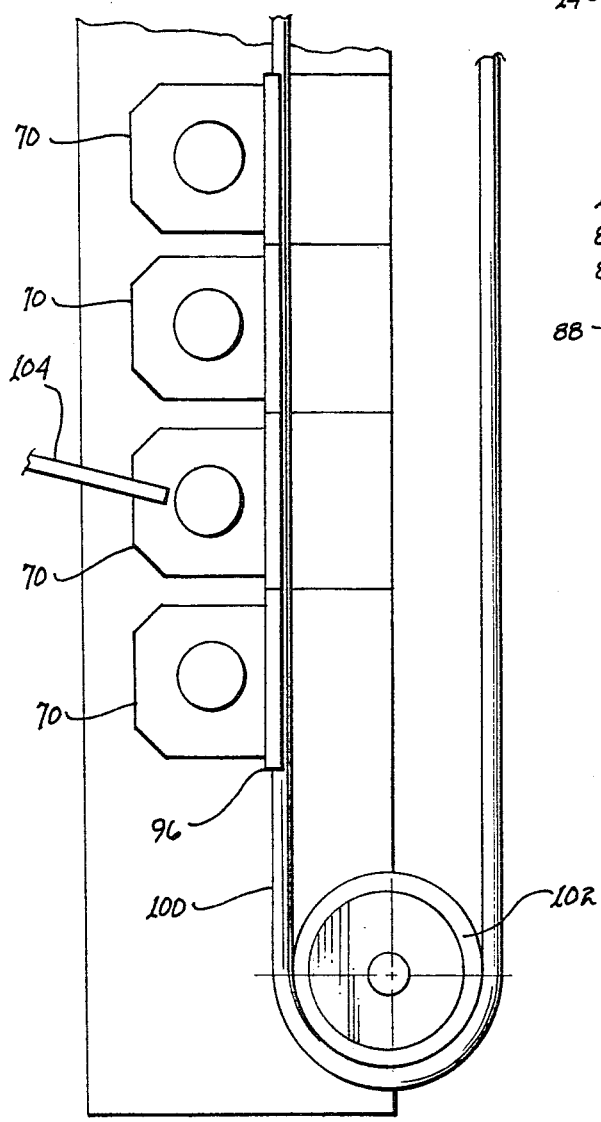
FIG. 6 is a pictorial illustration of a conveyor for the substrate holders.

FIG. 6 illustrates a representative apparatus for sequentially ejecting a plurality of solutions into the test and control cavities of each substrate mounted within serially aligned modules. In example, module 70, mounted within guide way 96, is incrementally translated past a discharge nozzle 104 by translation means (not shown). Simultaneous with the translation of module 70, drive belt 100 engages each wheel within each module to maintain the retained substrate in continuous spinning motion. As each module comes to and is momentarily stopped at discharge nozzle 104, a solution is discharged into the test and control cavities of the substrate. Thereafter, the module continues along guideway 96 to further discharge nozzles or other apparatus performing one of the steps of the testing process.

Before proceeding with a further discussion of the apparatus disclosed in the remaining drawings, it may be well to review the various steps for typing the blood sample.

Preparation of the substrate surfaces is very important in order to obtain sufficient reliability of the test process. The objective of such surface preparation is to ensure an adhesive-like bond between the substrate surface and the first monolayer of blood cells that will be laid onto the substrate surface. One such surface preparation is described to follow. Other forms of surface preparation may be provided onto the apparatus described in this disclosure.

Substrate plastic materials, such as polycarbonate, polystyrene, acrylic, mylar and others, appear to have an affinity (presumably by hydrophilic processes) for creating a reasonably strong bond with a layer of bovine serum albumin (hereinafter referred to as "BSA"). Accordingly, BSA is applied to first treat the surface. A solution of BSA, which is electronegative, is gently deposited on the surface of the test and control cavities by injection thereinto through a discharge nozzle 104 while the substrate is spinning. Thereafter, all excess BSA is washed away by injecting a quantity of normal saline solution through a nozzle. After washing, a transparent layer of BSA is formed on the cylindrical surfaces of the test and control cavities.

Thereafter, a solution of chromic chloride (hereinafter referred to as $CrCl_3$) is injected into the test and control cavities. The $CrCl_3$ solution is electropositive and will have an affinity for the BSA solution; it will also have an affinity for the red blood cells that will be subsequently placed within the test and control cavities. Excess $CrCl_3$ is rinsed away with a normal saline solution.

Figure 7:
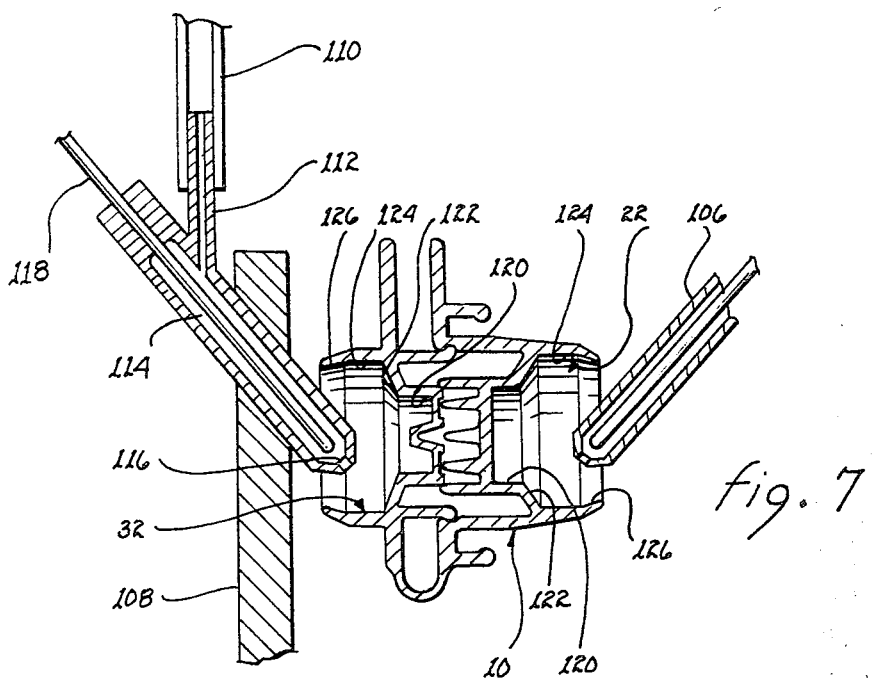
FIG. 7 illustrates apparatus for treating the substrate with fluids.

Referring to FIG. 7, there is shown apparatus for effecting the above described solution ejection steps. Substrate 10, being mounted within a module 70 (though not shown) is translated to a station placing the substrate intermediate discharge nozzles 104 and 106. These nozzles are brought into operative engagement with control cavity 32 and test cavity 22, respectively, by pivotal movement of a nozzle supporting arm, such as arm 108. Each nozzle includes a conduit 110 for conveying a solution from a source of solution to a feeder conduit 112 in fluid communication with chamber 114 and orifice 116. A plunger 118 is translatably locatable within chamber 114 to seal orifice 116 and thereby control discharge of the solution through the orifice.

Each of the two cavities in substrate 10 includes a base section 120, a radially sloping shoulder section 122, a wall section 124, which wall section is in alignment with the axis of rotation of the substrate and a radially inwardly oriented lip section 126. Since the inspection area of the blood sample to be inspected is essentially commensurate with wall section 124, any solution discharged within the cavity should not strike the wall section in order to prevent dislocation or non-continuity within any of the layers which are to be formed upon the wall section. Accordingly, discharge nozzles 104 and 106 are oriented such that any solution discharged through nozzle 116 will strike either base section 120 or shoulder section 122. Because of the centrifugal force imparted to any solution injected within the cavities, the solution will flow axially across wall section 124 and thereby minimize the disturbance to any existing layers thereupon. The slight radially inward orientation of lip 126 insures the formation of layers upon wall section without impeding washing and rinsing of excess solution from within each cavity. The extent of radial inwardness of lip 126 may advantageously be used to control the amount of liquid retained within each cavity.

Figure 8:
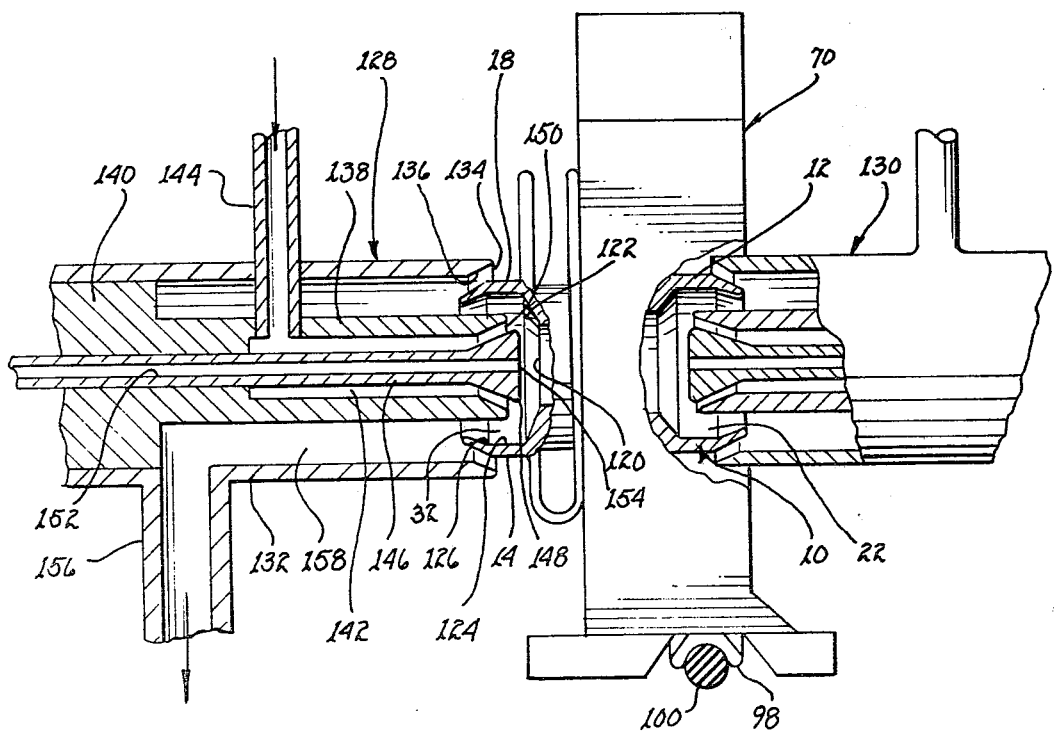
FIG. 8 illustrates apparatus for washing the substrate.

The washing or rinsing of substrate 10 may be accomplished with the apparatus illustrated in FIG. 8. Two water nozzles 128 and 130 are positionable by conventional mechanisms (not shown) to place the respective discharge orifices within cavities 32 and 22 of parts 14 and 12, respectively, of substrate 10. As both water nozzles are duplicates of one another, the following description will primarily be with respect to water nozzle 128, but it is to be understood that the description will apply equally well to water nozzle 130.

Water nozzle 128 includes a sleeve 132 having an opening 134 dimensioned to non-contactingly circumscribe cylindrical wall 18 of part 14. Interior edge 136 of opening 134 may be beveled, as shown, to accommodate any slight axial misalignment between the water nozzle and the substrate and to guide the sleeve on engagement with part 14. A nozzle 138 is disposed concentric with sleeve 132 and extends from a base 140 interior to the sleeve. The nozzle includes an axially centered cavity 142 in fluid communication with conduit 144, which conduit is connected to a source of fluid under pressure for metering the flow of fluid discharged from nozzle 138. A hollow stud 146 is mounted internal to cavity 142 in axial alignment therewith. The stud includes a cone-shaped end piece 148 for developing a cone-shaped spray pattern emanating from orifice 150 at the extremity of cavity 142. Passageway 152, extending through stud 146, is connected to a source of air under pressure for directing an air flow through orifice 154 in end piece 148. A drain conduit 156 is in fluid communication with annular space 158 disposed intermediate sleeve 132 and nozzle 138. To encourage the flow of fluid and air from within annular space 158 into drain conduit 156, a source of suction or low pressure may be connected to the drain conduit.

In operation, water nozzle 128 is brought into engagement with part 14 such that a lip section 126 is at least partly disposed within opening 134 in circumscribing relationship to nozzle 138. On initiation of fluid flow through conduit 44 and air flow through passageway 152, the cone-shaped spray of fluid will strike shoulder section 122 in cavity 32; whereby, the impact of the washing/rinsing fluid will not dislodge any existing layers already formed upon wall section 124. The air flow emanating from orifice 154 will strike base section 120 and result in turbulent air flow. The turbulent air flow, in combination with the low pressure environment within annular space 158 proximate to the edge of lip section 126, will tend to cause the discharged fluid to flow across wall section 124 and lip 126 into annular space 158. Therefrom, in combination with any inflowing air intermediate beveled edge 136 of opening 134 and the exterior surface of cylindrical wall of part 114, will encourage flow of the fluid into drain conduit 156. It may also be noted that during the wash/rinse operation, substrate 10 is spinning, which spinning action imparts a centrifugal force to the fluid to promote a smooth even depth flow across wall section 124 and lip 126. Simultaneous with the above described operation with respect to water nozzle 128, water nozzle 130 will operate in a similar manner to wash/rinse cavity 22 in part 12. After the surfaces in test cavity 22 and control cavity 32 have been prepared to receive and retain the red blood cell sample, the sample must be introduced to the prepared surfaces.

The introduction of the sample is effected by rupturing base sections 126 in each of cavities 22 and 32. Referring to FIG. 9, the apparatus for effecting such rupture will be described. Substrate 10 is mounted within and attached to wheel 72 of module 70 by circular flange 82 lockingly disposed within mating recess 86, as described above. In this position, flange 16 is brought into contacting supporting relationship with a mating supporting surface of the wheel. An axially translatable shaft 160 is positionally centered upon the axis of rotation of substrate 10. The shaft supports, through bearing 162, a cylindrical sleeve 164. The internal dimension of this sleeve is configured to circumscribe cylindrical wall 18 of part 14 such that edge 166 of the sleeve will bear against the surface of tab 26. As substrate 10 is spinning due to the interaction between drive belt 100 and wheel 72, bearing 162 is employed to allow sleeve 164 to rotate in response to frictional engagement with tab 26.

Figure 12:
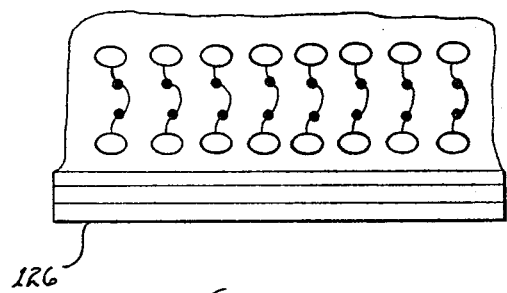
FIG. 12 is a cross-sectional view of substrate supported monolayers of red blood cells under test.

By axially translating shaft 160 by conventional means (not shown), part 14, by applying pressure against the surface of tab 26, is forced toward part 12. Such movement results in prongs 50 (see also FIGS. 1 and 2) to bear against and penetrate weakened areas 54 in base 126 of part 12; simultaneously, prongs 48 will bear against and penetrate weakened areas 52 in base 126 of part 14. The prong penetration of the weakened areas is illustrated in FIG. 12. As parts 12 and 14 are forced toward one another, the volume of sample compartment 24 will diminish and pressure will be exerted upon the sample disposed therein. As each set of prongs penetrate their respective weakened areas, the rupture occurring at the weakened areas will permit the red blood cell sample to flow through the resulting openings.

Due to the centrifugal force exerted upon the evacuated sample, the portion of the sample flowing into each of cavities 22 and 32 will flow onto shoulder section 122, wall section 124 and at least partly onto lip section 126. Any excess sample which is not contained by the somewhat radially inwardly oriented lip section will be discharged from the open end of the cavity.

Referring to FIG. 10, there is shown a substrate 10 wherein parts 12 and 14 have been physically forced toward one another until tab 26 is adjacent flange 16. By appropriate dimensioning, it may be noted that sample compartment 24 is essentially non-existant and all of the sample formerly contained therein has been discharged into cavities 22 and 32. Because of the sealed relationship of the prongs and ruptured weakened areas, the essential mating of the opposed sides of compartment 24 and the centrifugal force which urges flow of the sample to the radial extremities of the respective cavities, there exists very little probability of cross-flow of the sample from one cavity to the other. Should such flow occur, the integrity of the test and control samples would be lost. To further limit the probability of any cross-flow of the sample, the prongs and mating weakened areas can be somewhat modified to effect a seal at the ruptured openings. Such a seal is illustrated in FIG. 11.

The prongs, such as prong 50, instead of extending from a planar surface may be configured to extend from the planar surface of a square-shaped pedestal 168. Thereby, a planar surface circumscribing prong 50 and oriented orthogonal to the longitudinal axis of the prong is developed. Weakened area 54 may be manufactured to include a groove 170 in a square configuration duplicative of the four edges of pedestal 168 adjacent the base of the prong. Thereby, as tab 26 is forced adjacent flange 16, groove 170 will engage the corresponding edge 172 of pedestal 168 and effect a seal therebetween. The groove may also serve a secondary purpose of encouraging the folding back of ruptured sections 174 of weakened area 54. Alternatively, the groove may be replaced by a ridge to bear against the planar surface of the pedestal to effect a seal.

After the cavities in substrate 10 have been prepared by deposition of the BSA and CrCl$_3$ layers, the sample of red blood cells is deposited in the test and control cavities by operation of the apparatus described above. The red blood cells, which are electronegative, have an affinity for the chromic chloride and reasonably tight bonds will be formed therewith. Should a relatively thick layer of blood cells settle upon wall section 126, only those cells close to the surface of the wall section will have a chance to form bonds with the chromic chloride layer. A subsequent wash/rinse with a normal saline solution will remove all but the surface layer of the red blood cells. Such a layer is termed "monolayer" because only one layer of cells will remain after washing/rinsing.

Red blood cells are disc-like in shape and tend to lay flat on a surface. Being circular in shape, they do not cover a surface perfectly, but by simple calculation it is evident that approximately ninety percent coverage will occur.

An objective of the blood typing is to treat the sample of red blood cells with a known antibody and test for aglutination. The solution containing the known antibody is called "antiserum" or "antisera". A specific antiserum might be called "anti-A" because it contains antibodies that react with type A red blood cells. The antisera treatment procedure includes the step of applying the antisera with antibodies to test cavity 22 and the same serum but without antibodies to control cavity 32. Any excess serum in either cavity is discharged off the edge of lip section 126 by the rotary motion of the substrate. After a waiting period, the antibodies in the serum lodged within the test cavity will react with the antigens on the red blood cells therein to form bonds. If not antigens are present which are of the type that will react with the antibodies, no bonds will be formed.

The number of antigens of a given type on the surface of a red blood cell is variable. The presence of many antigens will produce a "strongly positive" reaction but to test for a weak reaction (i.e. few antigens) enough time must be allowed for a reaction to occur. To optimize the procedure, a greater concentration of antibodies in the antisera in the test cavity will optimize the treatment procedure.

If the membrane of a red blood cell ruptures, the red coloration (hemoglobin) will escape; this process is called "lysing". To lyse a cell means to bleach the cell of its red color. Lysing is accomplished by exposing red blood cells to an environment that is significantly less saline than normal blood as such a difference in salinity will cause rupture of the membrane. Distilled water, because it lacks salt, works very well for this purpose.

Bleaching or lysing of the red blood cell layer deposited on the chromic chloride layer is accomplished by introducing distilled water into test cavity 22 and control cavity 32 by means such as discharge nozzles 104 and 106. On contact with distilled water, the red blood cells will rupture the cell membranes and the hemoglobin will be released. The hemoglobin is rinsed away with a normal saline solution.

After lysing, the red blood cells will remain adhered to the chromic chloride layer but they are essentially transparent. These red blood cells are called "ghost cells"; however, they retain the antibody-antigen bonds formed during the antisera treatment procedure.

A second layer of blood cells is formed in the test and control cavity by applying a prepared amount of the reagent red blood cells to the wall sections of the two cavities. This second layer of red blood cells are known to react with or form a bond with the antibodies deposited upon the first layer of red blood cells. The antibodies thus act like a form of glue to bind the second layer of red blood cells with the antibodies. Necessarily, the absence of antibodies means that no bonding of the second layer will occur and subsequent testing for such bonding will produce a negative test result in the control cavity. Should there be no bonding between the first layer of red blood cells and, the antisera, either because of the absence of antibodies or because of no bonding between the first layer of red blood cells and the antibodies, the first and second layers will not be bonded to one another by the antisera. The test procedures to be later conducted will determine not only whether the second layer of red blood cells will adhere to the ghost cell layer but also how firm the adhesion may be.

Preparation of the second red blood cell solution may include the dilution of some of the sample red blood cells in a glycine saline solution. Glycine saline solution has a lower ionic strength than a normal saline solution which enables the red blood cells in solution to approach each other more closely. Specifically, the cells in the second blood cell layer can move closer to the ghost cells which allow the antibodies to attach more easily to an antigen on a cell in the second red blood cell solution. (The exact mechanism for this behavior is not clearly understood, but the effect appears to be as described.)

Preferably, a 20 to 1 solution of the red blood cells in a glycine saline solution is prepared. This ratio effectively reduces the volume of the red blood cells in solution to about 0.25%. The prepared solution is introduced to the test and control cavities to allow bonding with the layer of antisera.

To improve the adhesion of the second red blood cells to the ghost cells, it has been found that the addition of polyvinyl pyrrolidine (PVP) to the prepared solution has a beneficial effect. The PVP aids adhesion if it is going to occur but does not cause adhesion unless a reaction with an existing layer of antibodies will occur. The cause for this result is not clearly understood at the present time.

The PVP can be added either after the second layer of red blood cells is essentially formed or before the introduction of the second layer. A mixture of blood cells and PVP may also be used. To aid settling of the blood cells into a monolayer a centrifugal force (i.e. centrifuging) is applied by spinning the substrate 10. As the viscosity of PVP is relatively high the blood cells would otherwise remain suspended in PVP. Should the PVP be added after the second layer of red blood cells has formed a monolayer, care must be exercised during application of the PVP to avoid dislocation of the second layer of red blood cells. Because of the forces attendant the PVP due to the spinning substrate and the limited radial inward excursion of lip section 126, excess PVP will be automatically discharged from within the respective cavities.

The second layers of red blood cells in the test and control cavities are not lysed and they remain colored by the hemoglobin within the cells. The resulting effect is that of a light pink color visible to the eye. The absence of coloration would indicate that the second layer of red blood cells is absent.

To prepare the test and control cavities for inspection, the cavities are washed/rinsed to purge the cavities of any non-bonded second layer of red blood cells.

There are three primary methods for determining positive or negative results indicative of the presence or absence of a second layer of red blood cells. The first method entails visual inspection of the test and control cavities. The control cavity should appear to have a transparent mass deposited upon wall section 126. A pink color attendant wall section 126 of the test cavity would indicate the presence of a bonded second layer of red blood cells and the test would provide a positive result.

A second method contemplates the collection of the rinse solution from the test and control cavities. A subsequent test for optical density of the rinse is made by use of a spectrophotometer. A pink rinse from the test cavity would be indicative of a negative test result as the second layer of red blood cells would not have become bonded to the underlying layer of red blood cells.

A third method incorporates the washing of the cavities with a continuous flow of fluid while a change in the optical density (color) of each wall section is monitored. This method is performed by employing a light source and special optics for passing a beam of light through the wall sections to a detector. The output of the detector is chart recorded or may be used as data input to a data analyzer. The third method is of principal interest because it provides quantitative information directly from the wall sections under test. It also lends itself to automation. Moreover, the special optics required and attendant detection systems are well developed and are available from commercial sources. Finally, with the third method, the greater or lesser degree of existence of adhering red cells in the test cavity is an indicator of the degree of antigen-antibody reaction; and, the degree of adhesion, that is how rapidly the cells wash away, is an indication of the strength of the reaction.

Assuming a bonding occurs between the first and second monolayers of red blood cells and the sandwiched antibody the resulting structure will be similar to that illustrated in FIG. 12. That is, the layer of BSA on wall section 126 of the substrate will provide an adhering surface for the CrCl$_3$. The latter in turn acts as an adherent for the first monolayer of red blood cells (1-RBC). The antigens of 1-RBC will bond with the antibody and the latter will bond with the antigen of the second monolayer of red blood cells (2-RBC). Thereby, the two monolayers will sandwich the antibody therebetween.

Turning now to FIG. 13, there will be described apparatus for conducting the above described third method for inspecting substrate 10.

Water nozzles 176 and 178 are closely related in structure to earlier described water nozzles 128 and 130. Where common elements exist, like reference numerals have been employed. As stated above, the purpose for washing wall sections 126 in test cavity 22 and control cavity 32 is that of determining the color intensity and strength of the bond formed between the layers of bonded red blood cells. The purpose, of course, of employing a control cavity which purposely does not include bonds between the two red blood cell layers is to provide a basis for comparing the color and color persistence within the test cavity with that of the control cavity. Accordingly, agitation of the second red blood cell layer is welcomed.

A source of fluid under pressure is introduced through conduit 144 into annular cavity 142. A stud 180 is concentrically disposed within the annular cavity and includes a cone-shaped end piece 182 disposed at orifice 150 of the annular cavity. The flared end 184 of nozzle 138 in combination with end piece 182 produces a cone-shaped spray pattern which strikes shoulder section 122 within each of cavities 22 and 33. Therefrom, and because of the spinning motion of substrate 10, the fluid flows across wall section 126 onto lip section 124 and is discharged therefrom. A shroud 186 is concentric with cylindrical wall 18 of substrate 10 and includes radially inwardly oriented lip 188. The end of lip 188 is in close proximity to or lightly bears against the exterior surface of lip section 124 to effect a relatively good seal therebetween. Thereby, this seal, in combination with the vacuum developed within annular space 158 by the suction acting through conduit 156 will draw fluid off lip section 124 into conduit 156 with little leakage intermediate the substrate and shroud 186.

A source of light is introduced anterior of cavities 22 and 32 approximate to wall section 126 by light conductor 190. A mirror 192 or other means may be employed to direct the light essentially orthogonal to wall section 126. Any light passing through wall section 126 impinges upon mirror surface 194 or other reflecting means to direct the received light into light conductor 196. Both light conductor 190 and light conductor 196 may be attached to light conducting fiber optic cables 198 and 200. These cables in turn are connected, respectively, to a source of light and light detector means.

As discussed previously, a bar code or similar mechanically, electrically or optically readable identification indicia may be disposed upon flange 16 or tab 26 to identify each substrate. A sensor, such as sensor 202, may be attached to frame 204. The location of sensor 202 is commensurate with the position of the indicia upon either flange 16 or tab 26 such that as substrate 10 rotates, the indicia will travel past the sensor at each revolution. The information sensed or detected by sensor 202 is conveyed to appropriate deciphering equipment by conduit 206. To maintain homogeneity between the detection systems incorporated in conjunction with substrate 10, sensor 202 may be an optical detector which generates optical signals conveyed to deciphering equipment by a bundle of fiber optic elements disposed within or forming conduit 206.

It is to be understood that the previously described reverse typing, antibody screening, and compatability tests can also be performed by appropriate and described deposition of reagent and unknown red blood cells and reagent and unknown antibodies.

As will become apparent to those skilled in the art, complete testing of any given sample may become relatively laborious even with the automated apparatus described herein and will require the processing of a large number of substrates. To shorten the total time for conducting a large number of tests and to reduce the number of substrates which must be used, a somewhat differently configured substrate having pre-prepared bands of deposited monolayers of different, lysed reagent red blood cells may be developed. Thereafter, a known or unknown antibody is introduced, which antibody will bond to one or more of the bands, depending upon whether there does or does not exist a reaction between the antigens of the deposited red blood cells and the antibody. A second monolayer of reagent or unknown (depending upon whether the antibody is unknown or known, respectively) red blood cells are deposited upon the antibody to determine which bands exhibit a reddish color and thereby reflect bonding between the first and second monolayers. Analysis of these results will provide information pertinent to identification of the antibody or the second layer of red blood cells.

By employing the concept of multiple bands upon a substrate of monolayered reagent red blood cells wherein each band contains a different reagent red blood cell, a plurality of tests can be performed simultaneously with a known antibody and unknown second layer of red blood cells or a known antibody and an unknown second layer of red blood cells.

In one embodiment of substrate 10 which provides the capability of multiple simultaneous testing, both the test and control cavities could be in the form of elongated cylindrical surfaces separated by a diametric membrane and wherein the bands of the first monolayer of red blood cells have been deposited. Thereafter, the operation, as described above would be duplicated. It is envisioned that some modification of both the specimen injecting nozzles and the washing/rinsing nozzles might have to be effected to disperse the ejected fluids to all of the pre-prepared bands.

To reiterate, two of the prime objectives sought by and achieved by the apparatus described above is that of avoiding the need for technicians to laboriously conduct various blood related test procedures by hand and the resultant time delays and possibilities for error. Secondly, by spinning the substrate continuously during the whole test procedure, the centrifugal force created and acting upon the various fluids ejected upon the substrate uniformly disperses the fluids and tends to decrease the reaction times by one magnitude or more. An ancillary benefit of a centrifugal force, as determined by experimentation, is that of promoting and encouraging slow reactions which might be missed or misinterpreted were the test procedures performed manually. Thereby, the degree of confidence of the results achieved is increased over that of manual procedures.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:
1. Apparatus for diagnosing the reactions between layered fluids, said apparatus comprising in combination:
   (a) a substrate for providing a supporting surface for a plurality of fluids as each of the fluids is deposited thereon;
   (b) means for spinning said substrate to apply centrifugal force to the fluids deposited upon said substrate and urge each of the fluids into a layer;
   (c) means for ejecting each of the fluids upon said substrate while said substrate is spinning;
   (d) means for washing the layers of fluid while said substrate is spinning; and
   (e) means for inspecting a composite of layers of fluid to diagnose the reaction between layers of the fluids.

2. The apparatus as set forth in claim 1 wherein said substrate includes a test portion and a control portion.

3. The apparatus as set forth in claim 2 wherein said substrate includes a compartment for releasably storing a test sample of fluid.

4. The apparatus as set forth in claim 3 wherein said substrate comprises an open ended cylindrically shaped unit and including a diametrically extending central section defining said compartment and dividing said substrate into said test portion and said control portion.

5. The apparatus as set forth in claim 4 wherein said compartment includes pierceable membranes for accommodating flow of the test sample of fluid into each of said test and control portions.

6. The apparatus as set forth in claim 5 wherein said membranes comprise first and second opposed membranes and said compartment includes prongs for piercing said first and second membranes.

7. The apparatus as set forth in claim 6 wherein said first and second membranes include first and second sets of weakened areas and said prongs comprise a first set of prongs extending from said second membrane for piercing said first set of weakened areas and a second set of prongs extending from said first membrane for piercing said second set of weakened areas.

8. The apparatus as set forth in claim 7 wherein said substrate includes means for sealing said first and second membranes after said first and second membranes have been pierced.

9. The apparatus as set forth in claim 4 wherein said test portion and said control portion include cylindrical wall sections for receiving the layers of fluids.

10. The apparatus as set forth in claim 9 wherein said substrate includes a radially inwardly oriented lip section disposed adjacent one edge of each said wall section in proximity to the open ends of said test portion and said control portion for encouraging deposition of the layers of fluids upon said wall sections.

11. The apparatus as set forth in claim 10 wherein said substrate further includes a radialy inwardly oriented shoulder section disposed adjacent another edge of each of said wall sections.

12. The apparatus as set forth in claim 11 said ejecting means and said washing means include means for aiming said ejecting means and said washing means toward said shoulder sections.

13. The apparatus as set forth in claim 1 wherein said spinning means comprises a module for retainingly receiving said substrate.

14. The apparatus as set forth in claim 13 wherein said module comprises a frame, a rotatably mounted wheel disposed in said frame, retention means disposed within said wheel for retaining said substrate centered upon the axis of rotation of said wheel and means for engaging said wheel with a source of power to impart rotation to said wheel relative to said frame.

15. The apparatus as set forth in claim 1 wherein said ejecting means comprises a nozzle for ejecting a fluid onto the surface of said substrate.

16. The apparatus as set forth in claim 1 wherein said substrate comprises an open ended cylindrically shaped unit having a diametrically extending section dividing said substrate into a test portion and a control portion and wherein said ejecting means comprises a first nozzle for ejecting fluid into said test section and a second nozzle for ejecting fluid into said control section.

17. The apparatus as set forth in claim 1 wherein said washing means comprises a nozzle for ejecting washing fluid onto said substrate and said means for withdrawing the washing fluid from said substrate.

18. The apparatus as set forth in claim 1 wherein said substrate comprises an open ended cylindrically shaped unit having a diametrically extending section dividing said substrate into a test portion and a control portion and wherein said washing means comprises a first nozzle for ejecting a washing liquid into said test section and first means for evacuating the washing fluid from said test portion and a second nozzle for ejecting a washing fluid into said control section and second means for evacuating the washing fluid from said control portion.

19. The apparatus as set forth in claim 1 wherein said inspecting means comprises a light beam source, means for impinging the light beam from said source upon layers of fluid disposed on said substrate and means for analyzing the light beam acted upon by the inspected layers of fluid.

20. The apparatus as set forth in claim 1 wherein said substrate comprises a transparent cylindrically shaped unit having an inner wall for deposition of the layers of fluid and wherein said inspecting means comprises a source of light, means for directing light from said source radially through said cylindrically shaped unit to determine a change in characteristic of the light beam as a result of passage through the layers of fluid.

21. The apparatus as set forth in claim 20 wherein said inspecting means includes means for washing and rinsing the layers of fluid during inspection.

22. A spinnable substrate for supporting a plurality of layers of material to be inspected and useable in conjunction with a source of power for imparting a spinning motion to said substrate, said substrate comprising in combination:
(a) an hollow unit, said unit including an interior surface defining a locus of points about a longitudinal axis;
(b) means for attaching said substrate with the source of power to effect spinning motion to said substrate about the longitudinal axis of said interior surface; and
(c) opening means for receiving the material to be layered interior said substrate;
whereby, the material inserted interior said substrate becomes layered there against in response to the centrifugal force present upon spinning of said substrate.

23. A spinnable substrate as set forth in claim 22 wherein said interior surface is cylindrical.

24. A spinnable substrate as set forth in claim 22 wherein said unit comprises an open ended cylindrically shaped unit having a diametrically extending section dividing said substrate into a test portion and a control portion.

25. A spinnable substrate as set forth in claim 24 wherein each of said test portion and said control portion include interior cylindrical surfaces.

26. A spinnable substrate as set forth in claim 25 wherein said diametrically extending section comprises a compartment for storing a sample of material to be layered within said test portion and said control portion.

27. A spinnable substrate as set forth in claim 26 including means for establishing fluid communication between said compartment and said test and control portions.

28. A spinnable substrate as set forth in claim 25 wherein said attaching means comprises means concentric with said unit.

29. A spinnable substrate as set forth in claim 25 wherein said attaching means includes a flange radially extending from said unit.

30. A spinnable substrate as set forth in claim 29 wherein said attaching means further includes cylindrical means concentric with said unit extending from said flange.

31. A spinnable substrate as set forth in claim 22 wherein said hollow unit comprises:
(a) flange means having first and second sides;
(b) a first open ended cylinder extending from the first side of said flange means;
(c) a compartment disposed in the second side of said flange means, said compartment being in alignment with the longitudinal axis of said first open ended cylinder;
(d) a tab means having first and second sides;
(e) a second open ended cylinder extending from the second side of said tab means;
(f) means disposed in the first side of said tab means for sealing said compartment, said sealing means being in alignment with the longitudinal axis of said second open ended cylinder; and
(g) means for mating said sealing means with said compartment to bring the longitudinal axis of said first and second open ended cylinders coincident.

32. A spinnable substrate as set forth in claim 31 wherein each said first and second open ended cylinders includes a wall section and a radially inwardly extending lip section.

33. A spinnable substrate as set forth in claim 31 including means for establishing fluid communication between said compartment and said first open ended cylinder and between said compartment and said second open ended cylinder.

34. A spinnable substrate as set forth in claim 33 wherein said establishing means comprises prongs for piercing the walls of said compartment.

35. A spinnable substrate as set forth in claim 31 wherein said mating means comprises:
(a) a cylinder segment extending from the first side of said tab means concentric with said sealing means; and
(b) an annular recess disposed in the second side of said flange means concentric with said compartment for engagement with said cylinder segment.

36. A spinnable substrate as set forth in claim 34 wherein said mating means comprises:
(a) a cylinder segment extending from the first side of said tab means concentric with said sealing means; and
(b) an annular recess disposed in the second side of said flange means concentric with said compartment for engagement with said cylinder segment.

37. A spinnable substrate as set forth in claim 36 wherein said annular recess includes first engagement means for engaging said cylinder segment in a first position to define said compartment and second engagement means for engaging said cylinder segment in a second position to force piercing of the walls of said compartment by said prongs.

38. A spinnable substrate as set forth in claim 37 wherein said tab means and said flange means are interconnected.

39. A spinnable substrate as set forth in claim 38 wherein said hollow unit comprises a monolithic unit of synthetic plastic material.

40. A process for diagnosing the reactions between layered materials, said process comprising the steps of:
(a) providing a substrate for supporting each of a plurality of materials to be layered;
(b) spinning the substrate to impart a centrifugal force to any materials deposited and to be on the substrate and urge layering of the materials;
(c) depositing each of the materials upon the substrate;
(d) washing the material after deposition thereof on the substrate;
(e) inspecting the composite of layers of material deposited on the substrate to diagnose the reaction between the layers of material.

41. The process as set forth in claim 40 wherein the step of depositing includes the steps of:
(a) depositing a first layer of red blood cells upon the substrate;
(b) depositing a layer of fluid upon the substrate; and
(c) depositing a second layer of red blood cells upon the substrate.

42. The process as set forth in claim 41 including the step of storing a fluid to be tested in a compartment of the substrate and the step of depositing the stored fluid upon the substrate to become a layer of the composite layers to be inspected.

43. The process as set forth in claim 40 wherein said steps (c) and (d) are performed while the substrate is spinning.

44. The process as set forth in claim 40 including the step of preparing the substrate by applying at least one layer of material upon the substrate prior to exercise of steps (b)–(e).

45. The process as set forth in claim 40 wherein steps (c) and (d) are performed alternately until the composite of layers to be inspected is developed.

46. The process as set forth in claim 44 wherein the step of depositing includes the steps of:
(a) depositing a first layer of red blood cells upon the substrate;
(b) depositing a layer of fluid upon the substrate; and
(c) depositing a second layer of red blood cells upon the substrate.

47. The process as set forth in claim 46 including the step of storing a fluid to be tested in a compartment of the substrate and the step of depositing the stored fluid upon the substrate to become a layer of the composite layers to be inspected.

48. The process as set forth in claim 47 wherein said steps (c) and (d) are performed while the substrate is spinning.

49. The process as set forth in claim 40 including the steps of preparing the substrate prior to exercise of step (b) by depositing at least one layer of material on each of at least two discrete areas on the substrate.

50. The process as set forth in claim 49 wherein the step of depositing includes the steps of:
(a) depositing a first layer of red blood cells upon the substrate;
(b) depositing a layer of fluid upon the substrate; and
(c) depositing a second layer of red blood cells upon the substrate.

51. The process as set forth in claim 50 including the step of storing a fluid to be tested in a compartment of the substrate and the step of depositing the stored fluid upon the substrate to become a layer of the composite layers to be inspected.

52. The process as set forth in claim 51 wherein said steps (c) and (d) are performed while the substrate is spinning.

53. The process as set forth in claim 40 including the step of pre-preparing the substrate prior to exercise of step (b) by depositing within the substrate at least one layer of material.

54. The process as set forth in claim 53 wherein said step of pre-preparing comprises the step of depositing within the substrate at least one layer of material upon each of at least two different discrete areas of the substrate.

55. The process as set forth in claim 53 wherein the step of depositing includes the steps of:
(a) depositing a first layer of red blood cells upon the substrate;
(b) depositing a layer of fluid upon the substrate; and
(c) depositing a second layer of red blood cells upon the substrate.

56. The process as set forth in claim 55 including the step of storing a fluid to be tested in a compartment of the substrate and the step of depositing the stored fluid upon the substrate to become a layer of the composite layers to be inspected.

57. The process as set forth in claim 56 wherein steps (c) and (d) are performed while the substrate is spinning.

* * * * *